(12) United States Patent
Kosak (10) Patent No.: US 7,276,369 B2
(45) Date of Patent: Oct. 2, 2007

(54) METHOD FOR DETECTING A SUBSTANCE AND MICROTITER PLATE

(75) Inventor: Hans Kosak, Lisztstr. 15, 53115 Bonn (DE)

(73) Assignee: Hans Kosak, Bonn (DE)

( * ) Notice: Subject to any disclaimer, the term of this patent is extended or adjusted under 35 U.S.C. 154(b) by 0 days.

(21) Appl. No.: 10/479,368

(22) PCT Filed: May 29, 2002

(86) PCT No.: PCT/EP02/05910

§ 371 (c)(1),
(2), (4) Date: Jun. 14, 2004

(87) PCT Pub. No.: WO02/099417

PCT Pub. Date: Dec. 12, 2002

(65) Prior Publication Data

US 2004/0248117 A1    Dec. 9, 2004

(30) Foreign Application Priority Data

Jun. 2, 2001   (DE) ................. 101 27 045

(51) Int. Cl.
*C12M 1/34*   (2006.01)

(52) U.S. Cl. .................. 435/288.7; 435/283.1; 435/287.1; 435/287.2; 435/288.4; 422/50; 422/68.1; 422/61; 422/82.05

(58) Field of Classification Search ............ 435/4, 435/7.1, 174, 283.1, 285.2, 287.1, 287.2, 435/288.3; 422/50, 82.03, 82.06, 82.07, 422/82.05; 436/501, 518; 204/456
See application file for complete search history.

(56) References Cited

U.S. PATENT DOCUMENTS

| | | | | |
|---|---|---|---|---|
| 4,892,639 A | | 1/1990 | Sarrine et al. | |
| 5,348,633 A | * | 9/1994 | Karger et al. | 204/452 |
| 5,560,811 A | * | 10/1996 | Briggs et al. | 204/451 |
| 5,785,835 A | | 7/1998 | Saito et al. | |
| 6,203,679 B1 | * | 3/2001 | Bouis et al. | 204/466 |
| 6,214,187 B1 | | 4/2001 | Hammond et al. | |
| 6,414,306 B1 | * | 7/2002 | Mayer-Posner et al. | 250/288 |
| 6,562,213 B1 | * | 5/2003 | Cabilly et al. | 204/456 |
| 6,942,774 B1 | * | 9/2005 | Herbert | 204/456 |

FOREIGN PATENT DOCUMENTS

| | | |
|---|---|---|
| DE | 19948049 | 12/2000 |
| DE | 199 52 160 A1 | 5/2001 |
| WO | WO 01/16586 | 3/2001 |

* cited by examiner

*Primary Examiner*—Long V. Le
*Assistant Examiner*—Melanie J. Yu
(74) *Attorney, Agent, or Firm*—Fish & Richardson P.C.

(57) ABSTRACT

The invention relates to a method for detecting an analyte A in a liquid, comprising the following steps: (a) a solution containing an analytical reagent N is provided in a container B; (b) the analyte A is added to the solution, (c) an electrical field eF which acts upon the solution is applied by means of electrodes disposed outside the container B, whereby a modification occurs in the concentration of a substance which is specific with respect to the presence of the analyte A in a region M of the container B and (d) the modification of said concentration is optically detected.

7 Claims, 12 Drawing Sheets

SEQUENCE LISTING

<160> NUMBER OF SEQ ID NOS: 3

<210> SEQ ID NO 1
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 1
taacacaact ggtgtgctcc tgga                                    24

<210> SEQ ID NO 2
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 2
gagctaggac ctcttctgtc caggagcaca ccagttgtgt ta                42

<210> SEQ ID NO 3
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 3
tagggtcaat gccacccttt taacctatcc ggatttacg                    39

METHOD FOR DETECTING A SUBSTANCE AND MICROTITER PLATE

CROSS-REFERENCE TO RELATED APPLICATIONS

This application is a National Stage application under 35 U.S.C. §371 and claims benefit under 35 U.S.C. § 119(a) of International Application No. PCT/EP02/05910 having an International Filing Date of May 29, 2002, which claims benefit of DE 101 27 045.3 filed on Jun. 2, 2001.

The invention relates to a method for detecting an analyte, and to a microtiter plate suitable therefor.

The invention relates generally to the area of looking for and detecting pharmacological active ingredients. It is known in the art to bring a test substance or substances into contact with a plurality of different potential reactants for example in a microtiter plate. If the substance has an affinity for a potential reactant, a reaction takes place between the substance and the reactant. The reaction may be, for example, a chemical conversion or a binding. The reaction is detected by means of a change in the physical properties of the solution.

Detection methods used are for instance fluorescence polarization, fluorescence resonance energy transfer, fluorescence colleration spectroscopy and radiolabeling methods. The known detection methods are complicated. In some cases they require the use of poisonous substances.

Also known in the art are methods which enable a plurality of substance mixtures to be separated in parallel by electrophoresis. For example, Advanced Biotechnologies offers under the sign "Midge" an apparatus with which electrophoretic separation of up to 100 DNA samples in parallel is possible. For this purpose, each DNA sample is felt into a well of a gel. An electric field is then applied across the gel so that the samples are transported into the gel and fractionated there. Evaluation takes place via the distance the constituents of the DNA sample have migrated in the gel.—The known method is time-consuming.

DE 199 52 160 A1 discloses a method for detecting a first molecule in a solution, in which a dye-coupled second molecule can bind to the first molecule. The net electric charge on the second molecule is in this case smaller in size than and of opposite sign to the net electric charge on the first molecule. An anode and a cathode are present in the solution, and an electric field is applied between them. The dye is detected optically at the anode if the net electric charge of the first molecule is negative, and at the cathode if the net electric charge of the first molecule is positive. The method requires a complicated measuring apparatus in which a light beam must be focused exactly on the electrode in order to be able to detect the optical change at the electrode.

It is an object of the invention to eliminate the prior art disadvantages. It is particularly intended to indicate a method and a microtiter plate with which it is possible universally and without great effort simultaneously to investigate the reaction behavior of a plurality of substances.

According to the invention, a method for detecting a substance is provided having the following steps:

a) provision of a solution comprising a detection reagent in a container,
b) addition of the analyte to the solution,
c) application of an electric field acting on the solution by means of electrodes located outside the container, so that the concentration of an entity which is specific for the presence of the analyte changes in a region of the container, and
d) optical detection of the concentration change.

The proposed method is universal. It is simple to carry out. The use of hazardous or poisonous detection reagents is unnecessary. It is possible in particular to investigate simultaneously the effect of a large number of detection reagents on one analyte. The detection reagent is specific for the analyte. It reacts or binds with the analyte so that its electrophoretic mobility changes. It is particularly advantageous that, apart from the addition of the analyte in step b, no further addition to or removal from the container is necessary. It is possible thereby to avoid pipetting errors, and a high sample throughput is made possible. Since the electrodes are located outside the container it is possible to avoid electrolytic reactions at the electrodes. A further advantage is that exact focusing of a light beam on a predetermined point of the container is unnecessary for detection of the concentration change. The apparatus for optical detection of the concentration change can therefore have a simpler construction than an apparatus for detecting optical changes at an electrode.

The solution can be incubated after step b. The container, especially its wall or its base, preferably consists at least sectionally of an ion-conducting material and the electric field (eF) is applied in step c in such a way that a migration of ions in the material is brought about thereby. It is thus possible to achieve a concentration change specific for the analyte and optically detectable. The ions can moreover migrate out of the liquid into the material, out of the material into the liquid or through the material. No removal of liquid from the container is necessary for the optical detection of the concentration change in step d. The optical detection expediently takes place through the opening and/or the base of the container.

The entity is advantageously a detection reagent, a reaction product formed from the detection reagent and the substance, or a competitor. The detection reagent may additionally comprise a receptor, a competitor or a precursor of the reaction product. The receptor is expediently selected from the following group: peptide, protein, nucleic acid, sugar, antibody, lectin, avidin, streptavidin, PNA (peptide nucleic acid) or LNA (locked nucleic acid).

The entity may be labeled with a fluorophore. A possible example is a molecular beacon. The entity may be bound onto and/or in the base of the container.

For the optical detection of the concentration change, a light beam is passed at least through the region, and the change thereof brought about by the entity is measured. One possible light beam is a laser beam. Transmitted or reflected light can be utilized. The change brought about in the light beam may be a change in intensity, a change in the plane of polarization, a scattering angle or the like. The light beam is expediently guided so that it enters or emerges substantially perpendicularly from the base or the opening of the container. This simplifies the measurement. The method is thus suitable for standard microtiter plate readers.

In a particularly advantageous embodiment, the electric field is applied simultaneously across a plurality of containers. The optical detection of the concentration change in the plurality of containers can likewise take place simultaneously. The containers are expediently containers arranged in the manner of a microtiter plate on a common support.

Further according to the invention for carrying out the method a microtiter plate is provided with a plurality of containers which are formed at least sectionally of an ion-conducting material.—The use of an ion-conducting material makes it possible to bring about, through a migration of ions which is caused in the electric field, a concentration change which is specific for the analyte and which can be detected optically.

It is expedient for the walls and/or the base of the containers to be produced from the ion-conducting material. The base may be produced from an electrical insulator. It may also be activated for the binding of a ligand, receptor or substrate. However, it is also possible for a receptor or substrate to be immobilized on the base. In a further embodiment, different receptors can be immobilized on predetermined sections of the base. The base may be produced from glass, quartz or plastic.

The walls may consist of a porous material. They may be activated for the binding of a ligand. It is additionally possible for the walls to comprise auxiliaries, e.g. quenchers or protein- or nucleic acid-binding entities.

The containers may, according to a further embodiment feature, have a substantially rectangular cross section. In this case two walls of the container are arranged parallel to the electrodes. With such an arrangement, the electric field is developed homogeneously over the volume of the container.

The ion-conducting material may be produced from a material which is preferably selected from the following group: agarose, polyacrylamide, cellulose, paper, paperboard, porous silicate, polystyrene, polyvenyl chloride, polycarbonate, nylon, polyethylene. Other materials with ion-conducting properties are of course also suitable. The aforementioned materials are expediently in porous form.

In a particularly advantageous embodiment, the containers are in the form of recesses in a first plate produced from the ion-conducting material. The term "plate" is to be interpreted widely in this connection. It may also be a sheet or a layer applied to a support. The first plate may be put on a second plate which forms the base, and the first plate may produce the walls of the containers. The walls may be formed for example by the inner wall of perforations formed in the first plate. The second plate may be produced for example from glass or a transparent plastic. According to a further embodiment feature, a hydrophobic covering layer is applied to the first plate. This facilitates the filling of the containers. The hydrophobic material may be formed from a sheet which is expediently formed from an opaque material.

The ion-conducting material may be provided between two electrodes. The electrodes may be provided separately from the containers. The electrodes may be produced from conventional material such as, for example, silver, gold, platinum, copper, aluminum or electrically conducting plastic and the like. They may, for example, be attached to the ion-conducting material or be in ion-conducting contact therewith via an aqueous solution which permeates the ion-conducting material.

Exemplary embodiments of the invention are explained in more detail below by means of the drawings. These show.

Figure 1:
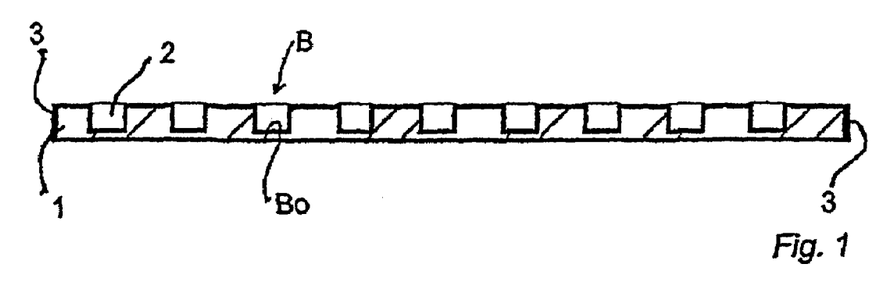
FIG. 1 a diagrammatic cross-sectional view of a first microtiter plate.

FIG. 1 shows a diagrammatic cross-sectional view of a first microtiter plate with a particularly simple design. This comprises a first plate 1 which has on one side a plurality of recesses 2. Each of the recesses 2 forms a container B for receiving a solution containing an analyte. The first plate 1 may consist for example of an agarose or polyacrylamide gel. Such gels can for example be cast in the form of conventional microtiter plates. It is also possible to produce the first plate 1 from ion-conducting material such as cellulose or derivatives thereof. The shaping can in this case take place by means of compression. The first plate 1 may moreover be produced from porous polystyrene, polyvenyl chloride, polyethylene, polycarbonate, polymethyl metacrylate, polypropylene and the like. It is possible in this case for the microtiter plate to be produced by the injection molding method. Reference number 3 designates the electrodes attached on the transverse sides of the first plate 1. The electrodes 3 can be produced from metals suitable for this purpose, such as platinum, gold, silver, an electrically conducting plastic and the like.

Figure 2:
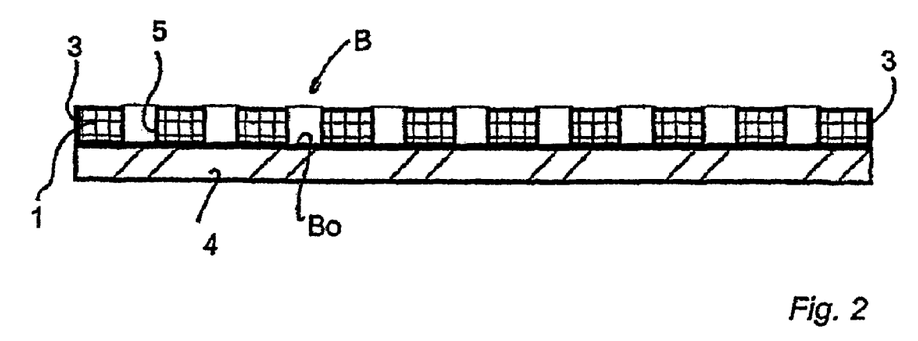
FIG. 2 a diagrammatic cross-sectional view of a second microtiter plate.

In the second microtiter plate shown in FIG. 2, the first plate 1 which is produced from ion-conducting material is placed on a second plate 4. The first plate 1 has in this case a plurality of perforations 5. The inner walls of the perforations 5 form the walls of the containers B. The base Bo thereof is formed by the side, facing the first plate 1, of the second plate 4. The second plate 4 can be produced for example from glass, quartz or polystyrene. It is expediently designed to be transparent. The second microtiter plate can be produced in a simple manner by casting an agarose gel for example on a glass plate. The perforations in the agarose gel can be produced by suitable plastic cores which have been previously placed on the glass plate and are removed again after solidification of the agarose or polyacrylamide gel.

For example detection entities such as peptites, proteins, nucleic acids and the like can be immobilized on the base Bo. It is also possible for the base Bo to be activated by chemical groups present thereon, such as aldehyde, epoxide, amino groups or biotin. The base Bo may, however, also be produced from an ion-conducting material.

Figure 3:
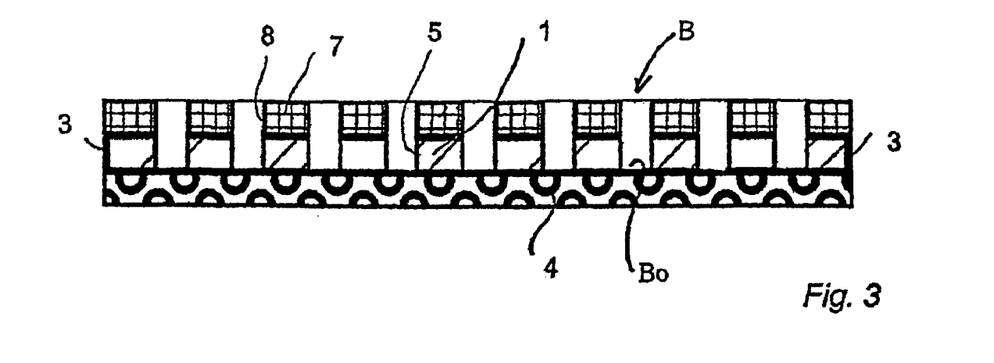
FIG. 3 a diagrammatic cross-sectional view of a third microtiter plate.
Figure 4:
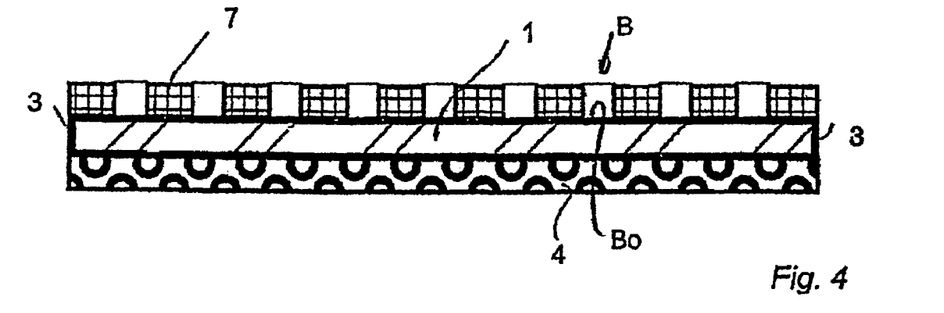
FIG. 4 a diagrammatic cross-sectional view of a fourth microtiter plate.
Figure 5:
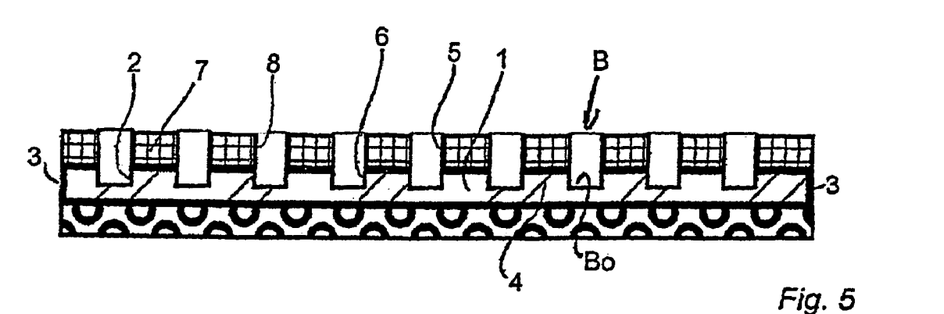
FIG. 5 a diagrammatic cross-sectional view of a fifth microtiter plate.

In the third, fourth and fifth microtiter plates shown in FIGS. 3 to 5, in each case a hydrophobic covering layer 7 is applied to the first plate 1. The hydrophobic covering layer 7 has two perforations 8 which correspond to the first perforations 5. In the fourth microtiter plate shown in FIG. 4, the first plate 1 has neither first recesses 2 nor first perforations 5. The first plate 1 in this case forms the base Bo of the containers B. In the exemplary embodiment shown in FIG. 5, first recesses 2 are provided in the first plate 1 and correspond to the second perforations 8 in the covering layer 7. The first perforations 5 correspond to the second recesses 6, so that recesses 6 form the lower part, i.e. a lower wall section and the base Bo, of the containers B.

Figure 6:
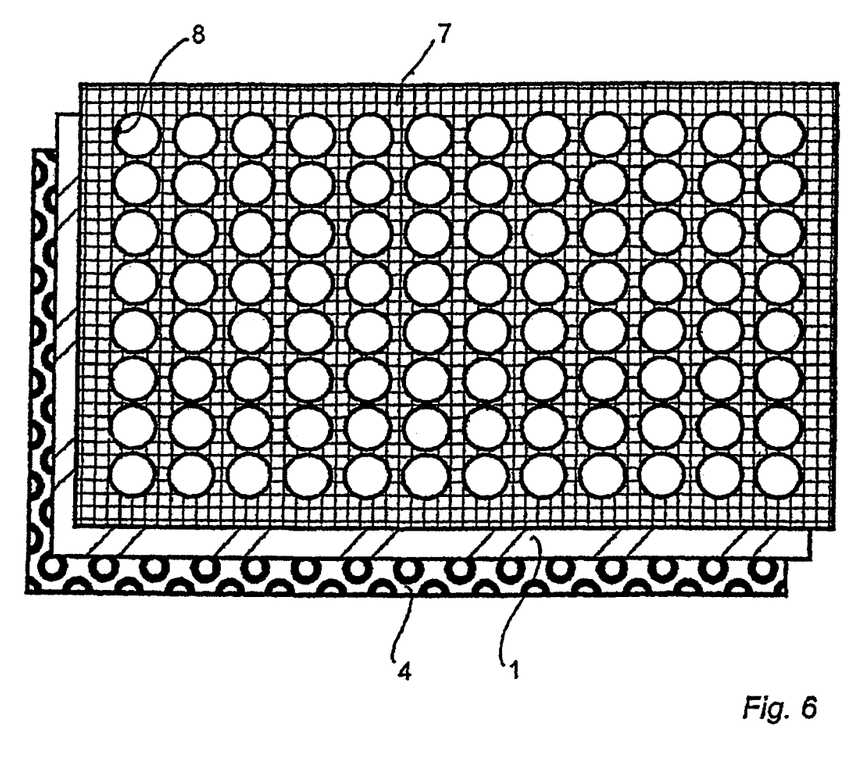
FIG. 6 a view from above onto the microtiter plate shown in FIG. 4.

FIG. 6 shows once again in a view from above the three-layer structure of the microtiter plate of the invention shown in cross section in FIGS. 3 to 5. The recesses 2, and first 5 and second perforations 8, can of course also be designed to be rectangular or square.

A subregion of the container B is shown in FIGS. 7 to 12. The container has an opening Op at the top and is bounded by wall W and base Bo. The walls W and/or the base Bo consist of an ion-permeable material. This material has the property, on contact with an electrolyte and on application of a voltage, of permitting an electrophoretic ion flux into the material. M designates the region of the container B which is encompassed by an optical measurement. The region M may include the base. The region M may be, for example, a central region of the container B.

Figure 7A:
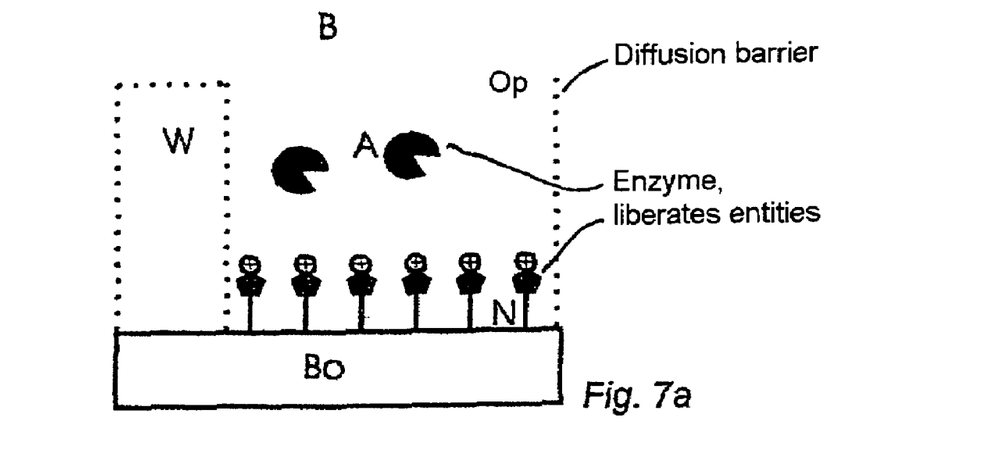
FIGS. 7a to c a first method variant.
Figure 7B:
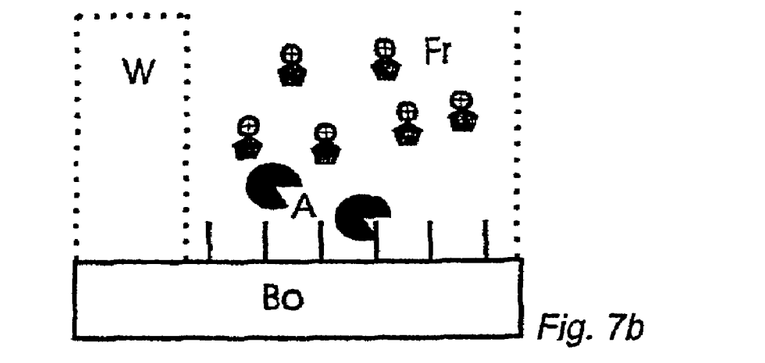
Figure 7C:
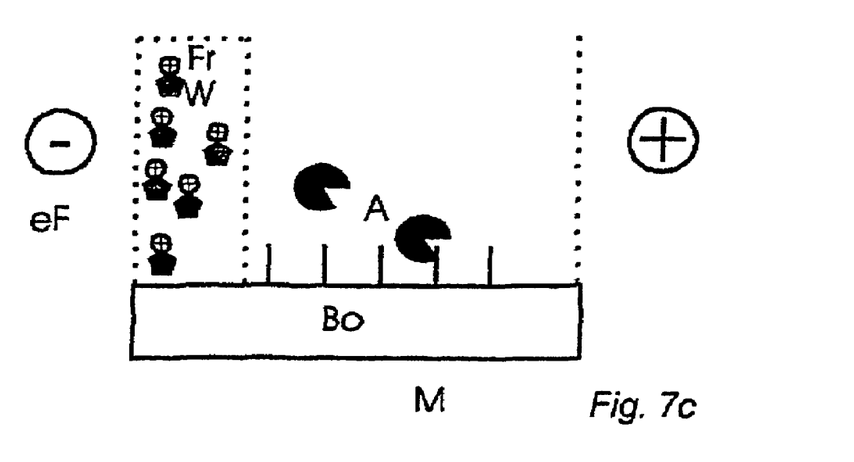

In the first method variant shown in FIGS. 7a to c, a detection entity N is bound to the base Bo. This may be, for example, a substrate for proteases or other lytic proteins. The detection entity N may be labeled for example by means of a fluorophore. An analyte is designated with the reference letter A. This may be for example a protease or other lytic proteins. On addition of the analyte A, the detection entity N is cleaved by the analyte and thus a fragment Fr is liberated. On application of an electric field (FIG. 7c), an electrophoretic force acts on the fragment Fr and the fragment Fr migrates into or onto the wall W of the container B. The concentration of the fragment Fr in the container B decreases. The fragment Fr has a label, e.g. a fluorophore, or can be detected optically because of other properties. The concentration of the fragment can be determined by means of a fluorescence measurement in the region M. In this arrangement, the decrease in fluorescence indicates the present of the analyte A to be detected.

Figure 7D:
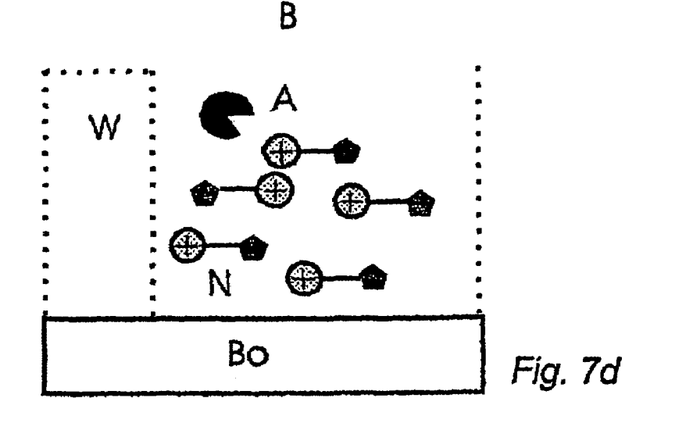
FIGS. 7d to f a modification of the first method variant.
Figure 7E:
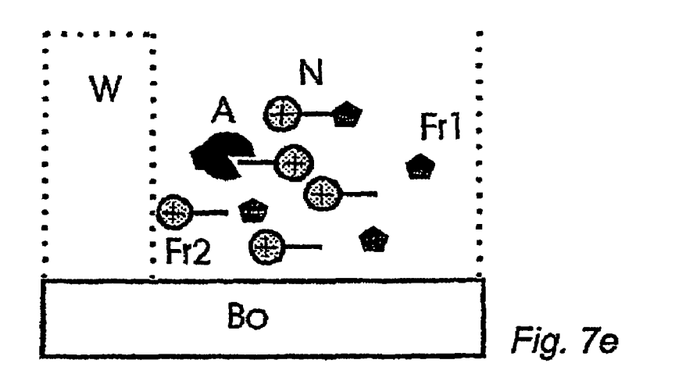
Figure 7F:
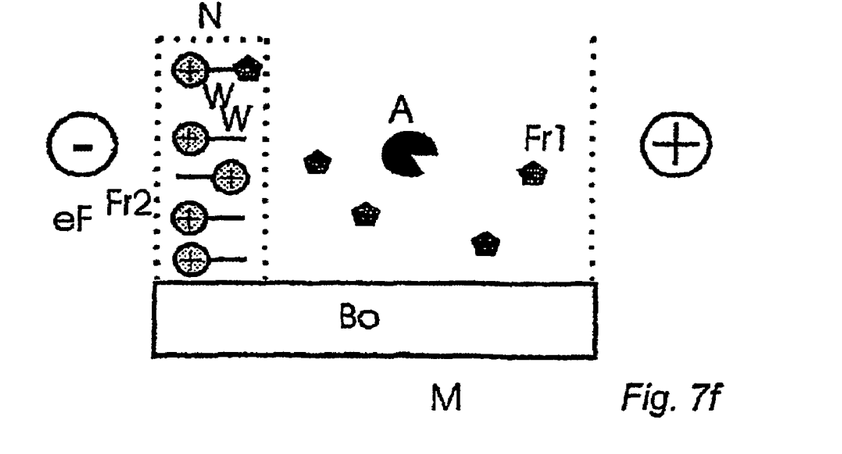

FIGS. 7d to 7f depicts a homogeneous method variant of the method described in FIGS. 7a to c. A charged and freely movable detection entity N is present in a container B. The detection entity N is charged and may be labeled for example by means of a fluorophore. The detection entity may be, for example, a substrate for proteases or other lytic proteins. An analyte A is brought into contact with the detection entity N. This may be for example a protease or other lytic proteins. On addition of the analyte A, the detection entity N is cleaved by the analyte A into two fragments Fr1 and Fr2. Fr1 is uncharged and can be detected optically for example through a fluorophore. Fr2 is charged. On application of an electric field (FIG. 7f) an electrophoretic force acts on the detection entity N and the charged fragment Fr2. Detection entity N and fragment Fr2 migrate into or onto the wall W of the container B. The uncharged fragment Fr1 remains in the container B. The concentration of the fragment Fr1 in the container is an indicator of the presence of the analyte A. The concentration of the fragment Fr can be determined by an optical measurement, for example a fluorescence measurement in the region M.

Figure 8A:
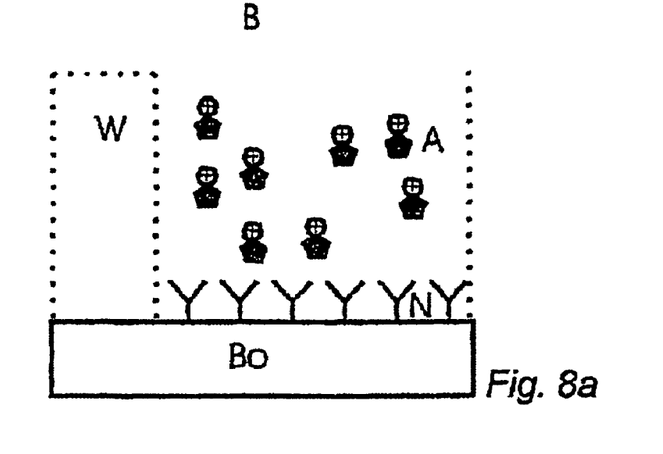
FIGS. 8a to c a second method variant.
Figure 8B:
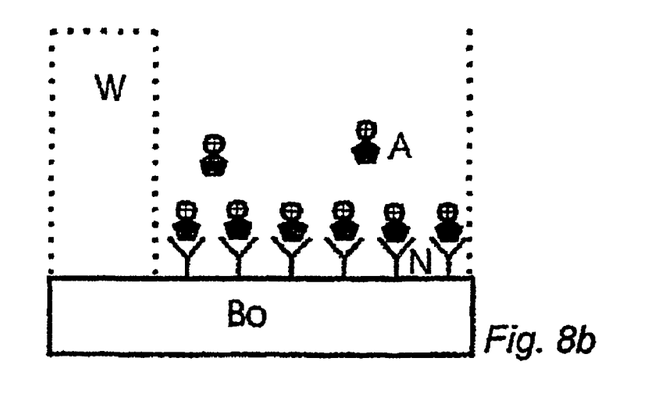
Figure 8C:
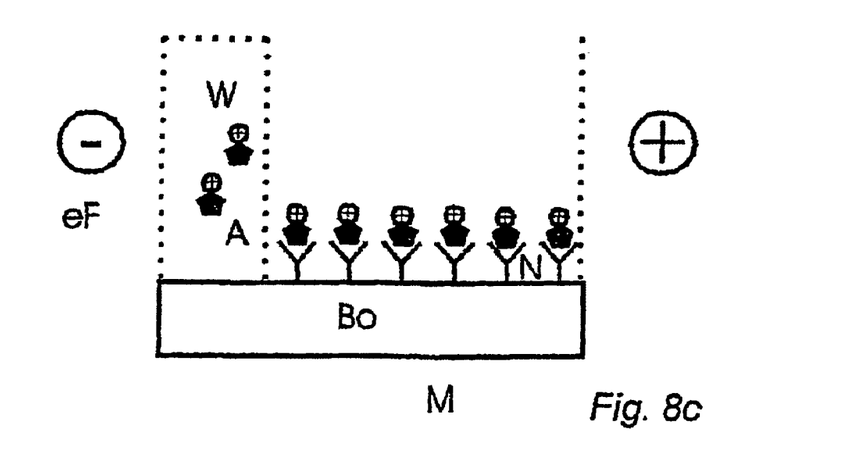

In the second method variant shown in FIGS. 8a to c, a detection entity N is bound to the base Bo of the container B. This is, for example, a ligand, an antigen, a receptor, an antibody or a nucleic acid. An analyte A is brought into contact with the detection entity N in a solution. The analyte A may be, for example, a receptor, an antibody, a ligand, an antigen or complementary nucleic acid. The analyte A binds to the detection entity N. The analyte A is labeled for example by means of a fluorogen F. On application of an electric field, the analyte A migrates into the ion-conducting wall W. If the detection entity N is specific for the analyte A, part of the analyte A binds to the detection entity N. The binding of the analyte A to the second detection entity N can be detected by means of a fluorescence signal due to the fluorophore F.

Figure 9A:
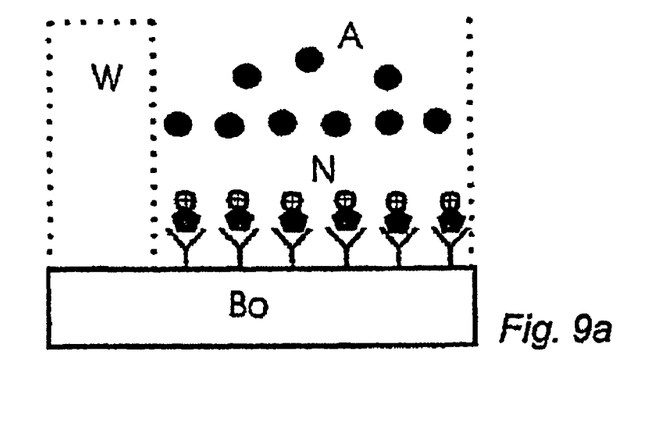
FIGS. 9a to c a third method variant.
Figure 9B:
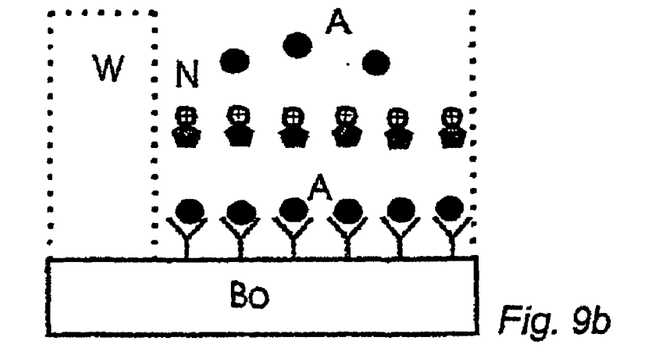
Figure 9C:
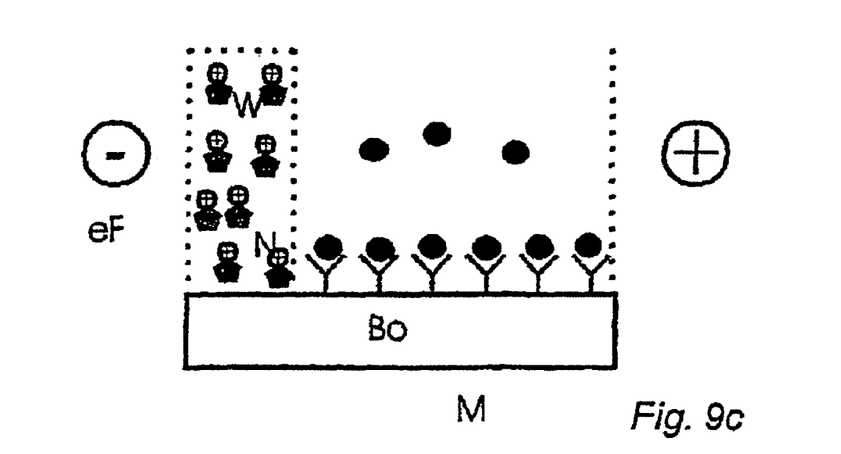

In the third method variant shown in FIGS. 9a to c, an analyte A displaces a detection entity N from its binding to a defined binding site. The binding of the analyte A and the binding of the detection entity N is specific in each case. The binding site may be, for example, an antibody immobilized on the base Bo or an immobilized nucleic acid. The detection entity N may be a specific antigen or a complementary nucleic acid. Displacement of the detection entity N by the analyte A results in free mobility of the previously immobilized detection entity N. The detection entity N is charged. Application of an electric field moves the detection entity N into or onto the ion-permeable wall W. The concentration of the detection entity N is found by an optical measurement in the region M. The decrease, observable in this case, of a previously present fluorescence signal is specific for the presence of the analyte A in the solution.

Figure 10A:
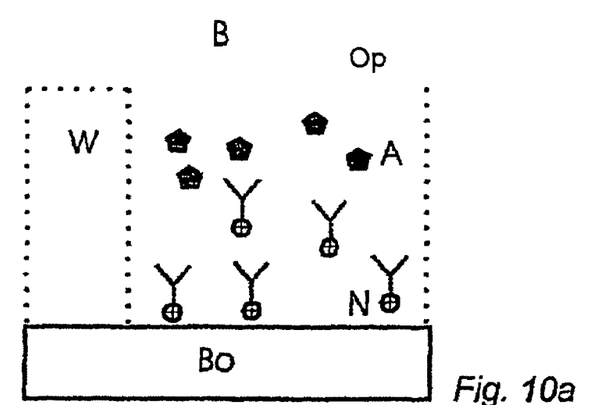
FIGS. 10a to c a fourth method variant.
Figure 10B:
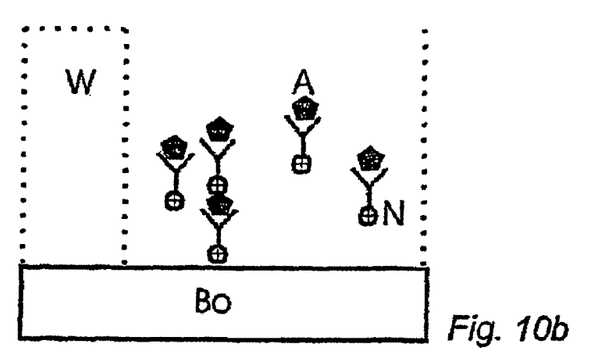
Figure 10C:
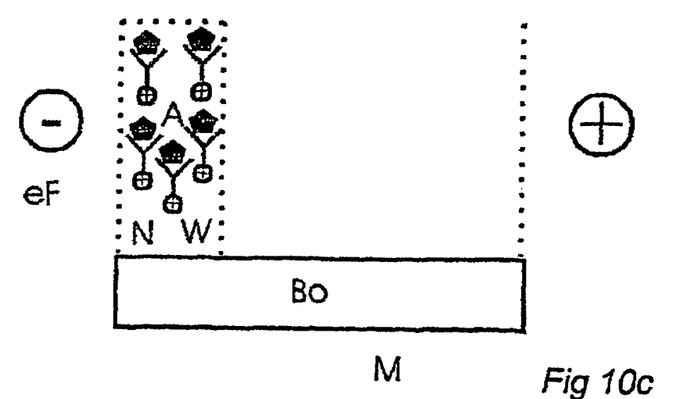

In the fourth method variant shown in FIGS. 10a to c, an analyte A and a charged and freely mobile detection entity N is present in the container B. The analyte A is labeled for example by means of a fluorophore. On addition of the analyte A there is a binding, specific for analyte A, with the detection entity N. Application of an electric field moves the charged detection entity N and the analyte A bound thereto into or onto the ion-permeable wall W outside the region M. The decrease in the concentration of the fluorescent analyte A in the container B can be detected by fluorimetry in the region M.

Figure 11A:
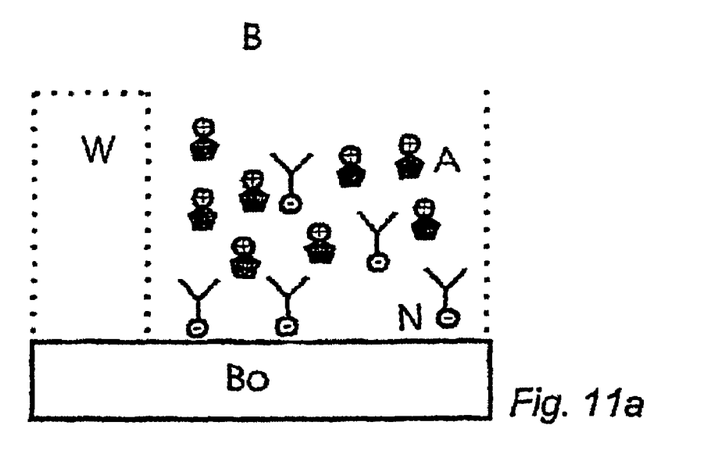
FIGS. 11a to c a fifth method variant.
Figure 11B:
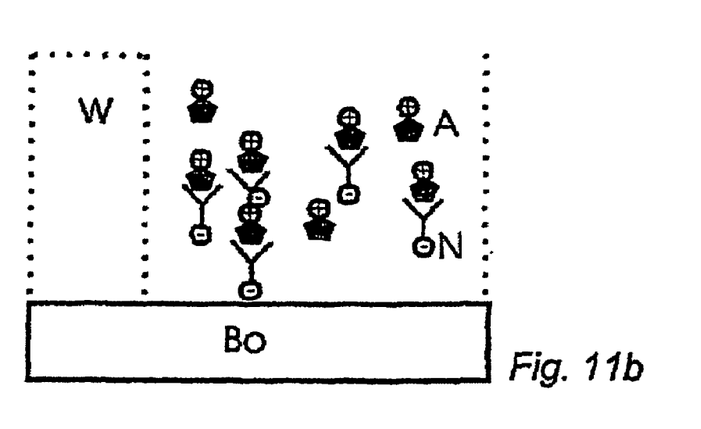
Figure 11C:
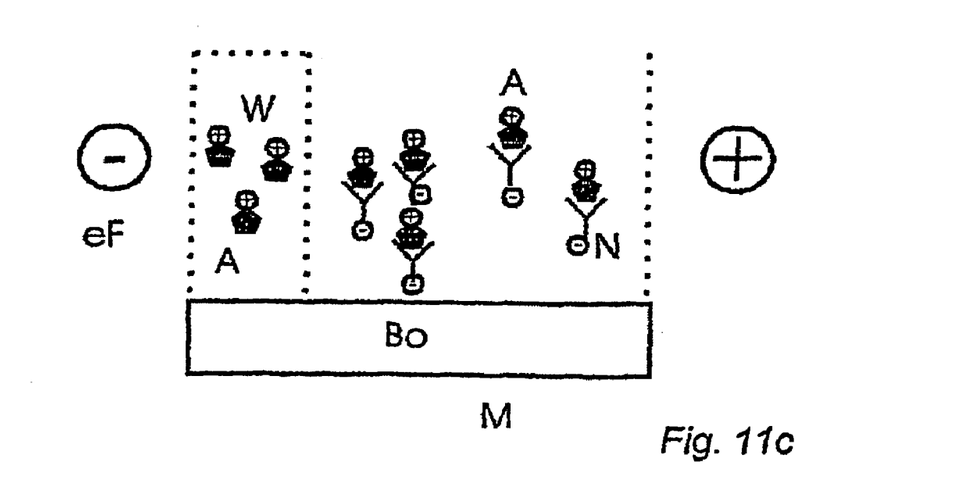

In the fifth method variant shown in FIGS. 11a to c, a positively charged analyte A and a negatively charged detection entity N is present in the solution. The analyte A is labeled for example by means of a fluorophore. On addition of the analyte A there is a binding, specific for analyte A, with the detection entity N. Binding of the analyte A to the detection entity N makes the total charge of the complex zero. On application of an electric field eF, the uncharged complex of detection entity N and analyte A bound thereto remains in the container B. Unbound analyte A is moved into or onto the ion-permeable wall W. The diminished decrease in the concentration of the fluorescent analyte A in the container B compared with a sample without detection entity N can be detected by fluorimetry in the region M. The diminished decrease indicates the presence of the analyte A.

Figure 12A:
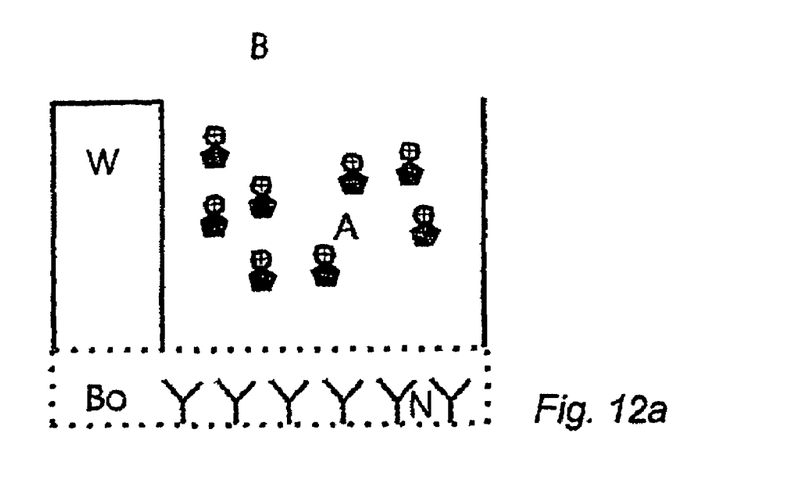
FIGS. 12a to c a sixth method variant.
Figure 12B:
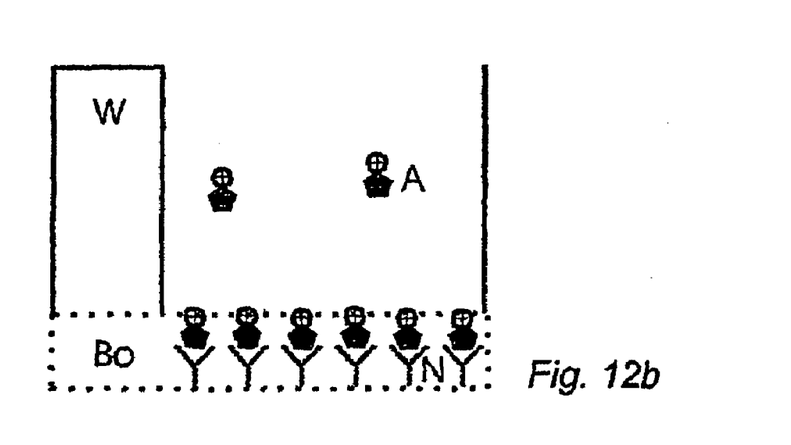
Figure 12C:
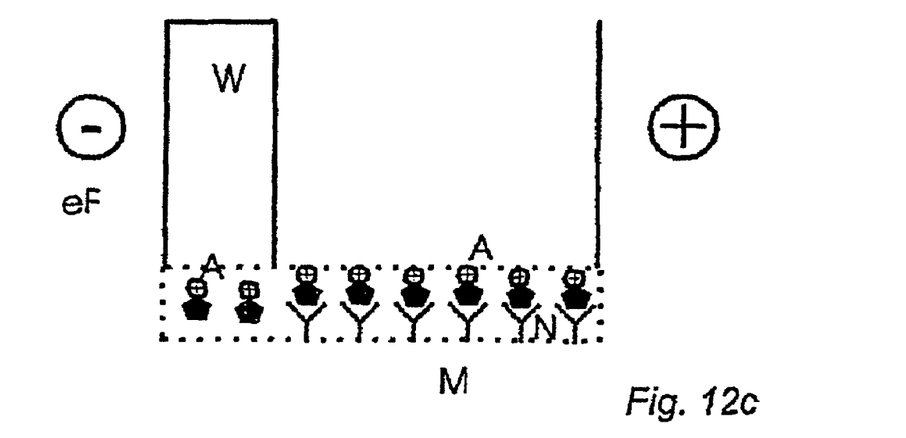

In the sixth method variant shown in FIGS. 12a to c, the base Bo of the container B is ion-permeable. In addition, a first detection entity N is bound in the base Bo. The base Bo may consist for example of activated agarose or polyacrylamide to which antibodies or nucleic acids have been bound as detection entity N. A charged analyte A is introduced into the container B. The analyte A may be labeled for example by means of fluorophore. The analyte A comes into contact with detection entity N through diffusion or through application of an electric field eF. The contact results in a specific binding between analyte A and detection entity N. Application of an electric field eF moves unbound analyte A out of region M, which is detected in an optical measurement. Only the bound analyte A is detected in an optical measurement of the region M. The fluorescence in region M is an indicator of the presence of the analyte A to be detected.

Figure 13:
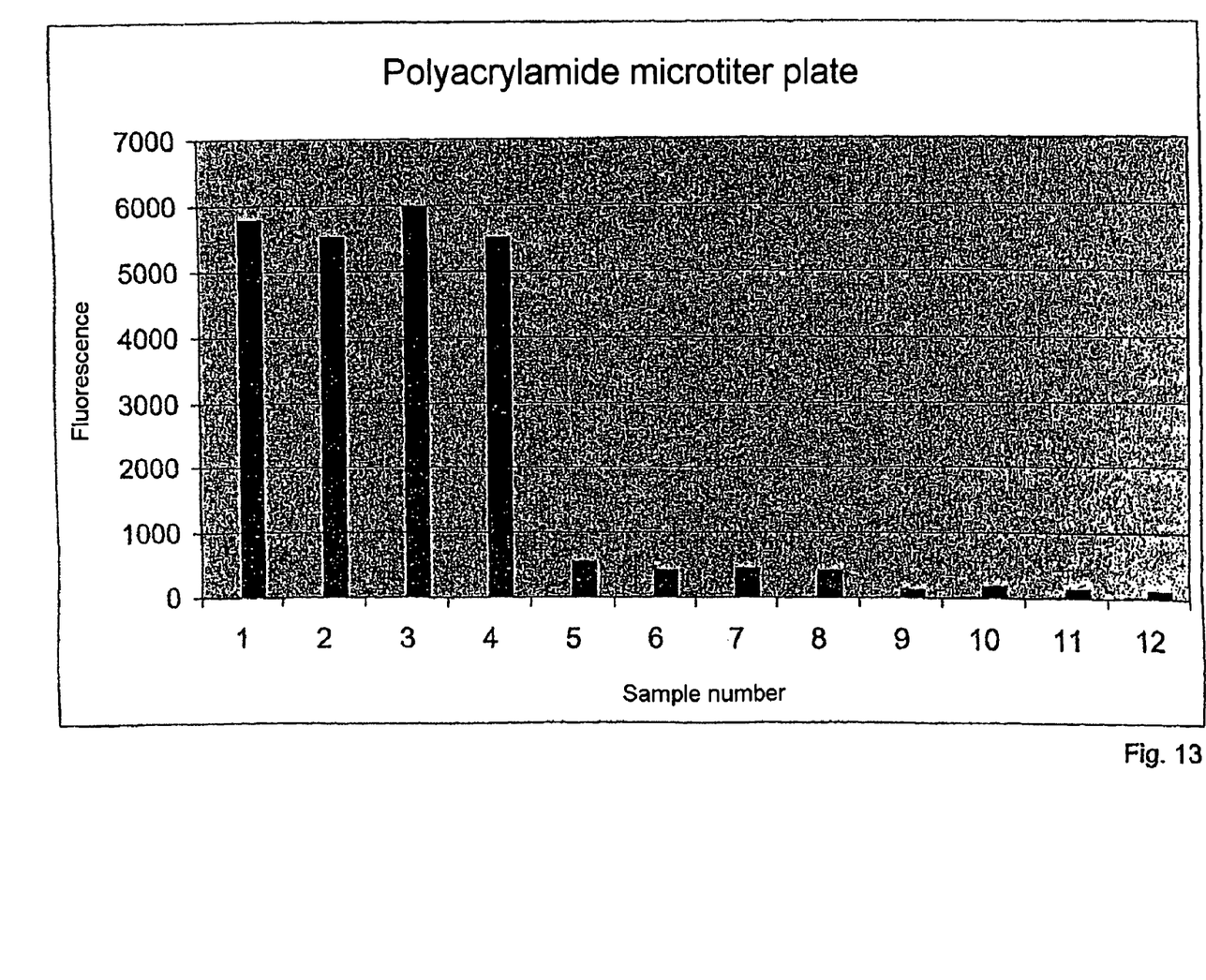
FIG. 13 a fluorimetric evaluation using a polyacrylamide microtiter plate.

FIG. 13 shows a fluorimetric evaluation using a microtiter plate of the invention produced from polyacrylamide. A microtiter plate fluorescence reader is used for the evaluation. Immobilized oligonucleotide A of sequence 5'-TAA CAC AAC TGG TGT GCT CCT GGA-3' (SEQ ID NO: 1) was present in all the samples 1 to 12. Samples 1 to 4 are in contact with TAMRA-labeled oligonucleotide A' of sequence 5'-TAMRA-GAG CTA GGA CCT CTT CTG TCC AGG AGC ACA CCA GTT GTG TAA-3' (TAMRA-SEQ ID NO: 2) which is complementary at its 3' end to the immobilized oligonucleotide A. Samples Nos. 5 to 8 are in contact with TAMRA-labeled oligonucleotide K of sequence 5'-TAMRA-TAG GGT CAA TGC CAC CCT TTT AAC CTA TCC GGA TTT ACG-3' (5'-TAMRA-SEQ ID NO: 3), which is not complementary to oligonucleotide A. Samples Nos. 9 to 12 merely contained buffer. The fluorescence is shown here in arbitrary units.

Figure 14:
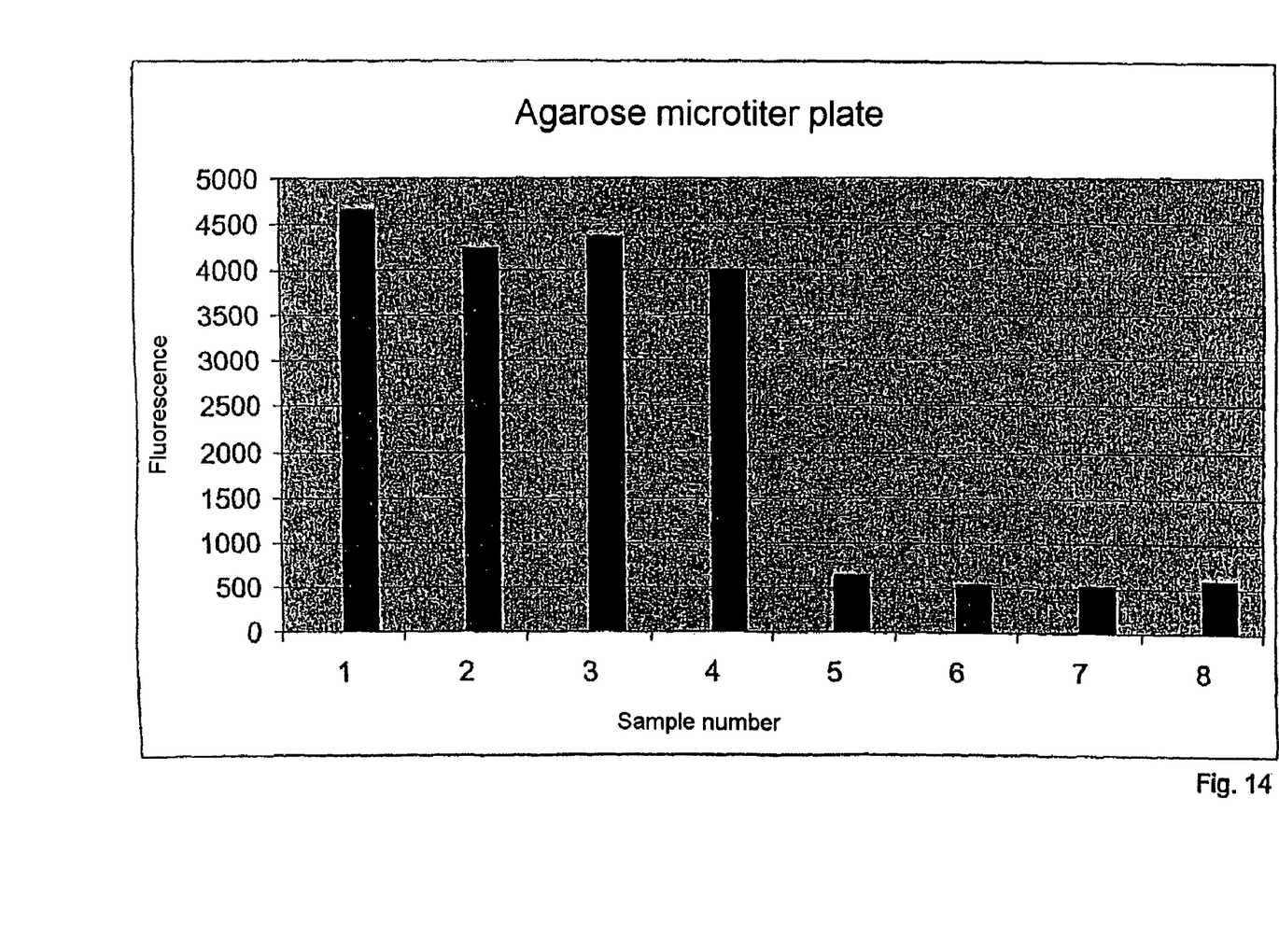
FIG. 14 a fluorimetric evaluation using an agarose microtiter plate.

FIG. 14 shows the results of a fluorimetry evaluation using a microtiter plate of the invention produced from agarose. TAMRA-labeled oligonucleotide A' was present in all the samples. Samples Nos. 1 to 4 are in contact with RecA protein. Samples Nos. 9 to 12 contained only buffer. The fluorescence is shown in arbitrary units.

The detection can be carried out considerably more quickly by applying an electric field. The fluorescence can be detected immediately in the predetermined region of the container. The region may be a central region of the container, a region in the vicinity of a wall, or the base of the container.

EXAMPLES

1. Production of a Supported, Ion-Conductive, Polyacrylamide-Based Microtiter Plate with Detection Entities.

A cassette consisting of two glass plates and 1 mm Teflon spacers with the internal volume 1 mm×80 mm×120 mm was provided on the inner sides of each of the glass plates with a plastic support (Gelbond PAG Film, Pharmacia-Amersham), which are suitable for covalent coupling to acrylamide. A plastic support was provided with rows and columns of square recesses which were each 2 mm×2 mm in size and were each 9 mm apart. The recesses were produced with the aid of a cutting blotter (Graphtec). A solution of 20% acrylamide with a monomer to crosslinker ratio of 29:1 was prepared in 1×TBE buffer. Acrydite oligonucleotides A (Eurogentec, Belgium) were added in a concentration of 10 µmol/l as detection entity before the polymerization. To start the polymerization, 70 µl of 10% (w/v) fresh ammonium persulfate and 20 µl of TEMED was added, and the solution was poured into the cassette. After one hour, the glass plates were removed and the microtiter plate was placed in a slab electrophoresis chamber with the plastic support with the recess on top. Unbound charged constituents were removed by subjecting the microtiter plate to an electrophoresis in 1×TBE at 100 V for one hour.

2. Procedure for a DNA Hybridization Assay Using the Polyacrylamide-Based Microtiter Plate 2 µl portions of sample solution in 1×TBE buffer were put into the recess of the microtiter plate. Four sample solutions in each case contained:
a) 10 pmol of the TAMRA-labeled oligonucleotide A' prepared by TibMolbiol, Berlin, with the sequence complementary to oligonucleotide A.
b) 10 pmol of the TAMRA-labeled oligonucleotide K, prepared by TibMolbiol, Berlin, and
c) no oligonucleotide Oligonucleotide A' and K were labeled at the 5' end with a fluorophore (TAMRA). The microtiter plates were brought into contact with TBE buffer on the sides facing the electrodes, and the microtiter plate was subjected to an electrophoresis at 50 V for 10 minutes.

3. Fluorimetric Evaluation of the DNA Hybridization Assay

The microtiter plate was inserted into a microtiter plate reader (Lambda 320, MWG-Biotech), and the fluorescence of the recess was measured. The fluorescence was determined with excitation at 540 mm and emission at 590 nm in reflected light mode. The fluorescence in the samples with oligonucleotide A' was distinctly increased compared with the fluorescence of the samples with oligonucleotide B and the pure TBE sample. The increased fluorescence of the sample with oligonucleotide A' indicates the specific binding of oligonucleotide A' to the Acrydite oligonucleotide A.

4. Production of a Supported, Ion-Conductive, Agarose-Based Microtiter Plate

Two combs each with four shaping cores of Teflon were suspended 9 mm apart 1 mm above the base in a chamber consisting of a glass plate with tightly surrounding rims of dimension 80 mm×40 mm. The edge length of the square shaping cores was 2 mm×2 mm in each case. The shaping cores were 9 mm apart. A 2% agarose suspension in TBE buffer was heated in a microwave until the agarose was completely swollen, and about 12 ml of the suspension was poured into the chamber. After the agarose had solidified, the shaping cores were removed. An arrangement of 2×4 recesses with a square opening of 2 mm×2 mm and a depth of about 3 mm had been produced by means of the shaping cores in the produced microtiter plate. An opaque plastic sheet with recesses was placed on the solidified agarose in such a way that the recess in the sheet coincided with the recesses in the agarose.

5. Procedure for a DNA-Protein Binding Assay Using the Agarose-Based Microtiter Plate.

8 µl of a solution of TBE, 10 µmol/l $MgCl_2$ and, as detection entity, 10 µmol/l oligonucleotide K were introduced into each of the eight recesses in the microtiter plate. Oligonucleotide K was provided with a fluorophore (TAMRA) at the 5' end for labeling. 4 µl of RecA protein (Roche) of a concentration of 1 µg/µl in RecA buffer (10 mmol/l Tris Cl, 10 mmol/l $MgCl_2$, 1 mmol/l DTT, pH 8) was added as sample into each of four recesses. The same volume of RecA buffer without RecA protein was introduced as negative control into the remaining four recesses. The microtiter plate was incubated at 37° C. for 30 min and then exposed to an electrophoresis at 50 V for 10 min.

6. Fluorimetric Evaluation of the Protein-DNA Binding Assay

The microtiter plate was inserted into a microtiter plate reader (Lambda 320, MWG-Biotech) and the fluorescence was measured in the region of the recess. The fluorescence was determined with excitation at 540 mm and emission at 590 nm in reflected light mode. The fluorescence in the samples with RecA protein was distinctly increased compared with the fluorescence of the samples without RecA protein. The increased fluorescence of the sample with RecA protein indicates the change in the electrophoretic mobility of binding of oligonucleotide K owing to the binding of RecA protein to oligonucleotide K.

LIST OF REFERENCE SYMBOLS 1 first plate
2 first recess
3 electrode
4 second plate
5 first perforation
6 second recess
7 hydrophobic covering layer
8 second perforation
B container
Bo base
A analyte
N detection entity
eF electric field
M region of the container whose optical change is detected
W wall

The invention claimed is:

1. A method for detecting the presence of an analyte in a liquid comprising the steps of:
   (a) providing a solution comprising a detection reagent in a container, wherein the container consists of an opening, a wall, and a base, wherein the wall or the base or a section of the wall or the base consists of an ion-conducting material such that ions can migrate out of the liquid into the material or through the material when an electric field acting on the solution by means of electrodes located outside the container is applied,
   (b) adding the analyte to the solution followed by incubating the solution,
   (c) applying an electric field on the solution by means of electrodes located outside the container in such a way that ions migrate out of the liquid into the material or through the material, and the migration of ions causes a concentration change of an entity in a region of the container, wherein the entity is the detection reagent or a reaction product formed from the detection reagent and the analyte, and the region of the container is defined by the opening, the wall and the portion of the base positioned below the opening, and
   (d) detecting the presence of the analyte by optically detecting the concentration change of the entity during or after the applying an electric field of step c), wherein detection is performed through the opening and/or the portion of the base positioned below the opening of the container, where a light beam is passed at least through the region and where the light beam is guided so that it enters the portion of the base positioned below the opening of the container or the opening, or emerges from the portion of the base positioned below the opening of the container or the opening, perpendicularly to the base or the opening.

2. The method as claimed in claim 1, where the detection reagent comprises a receptor, a competitor, or a precursor of the reaction product.

3. The method as claimed in claim 2, where the receptor is selected from the following group: peptide, protein, nucleic acid, sugar, antibody, lectin, avidin, streptavidin, PNA or LNA.

4. The method as claimed in claim 1, where the entity is labeled with a fluorophore.

5. The method as claimed in claim 1, where the entity is bound onto and/or in a base of the container.

6. The method as claimed in claim 1, where the electric field is applied simultaneously across a plurality of containers arranged in succession.

7. The method as claimed in claim 6, where the optical detection of the concentration change takes place simultaneously in the plurality of containers.

* * * * *